(12) United States Patent
Labarthe

(10) Patent No.: US 10,814,063 B2
(45) Date of Patent: Oct. 27, 2020

(54) METHOD AND DEVICE FOR DETECTING AN OCCLUSION IN AN INFUSION LINE

(71) Applicant: Fresenius Vial SAS, Brézins (FR)

(72) Inventor: Sebastien Labarthe, Voiron (FR)

( * ) Notice: Subject to any disclaimer, the term of this patent is extended or adjusted under 35 U.S.C. 154(b) by 134 days.

(21) Appl. No.: 15/736,515

(22) PCT Filed: Jun. 9, 2016

(86) PCT No.: PCT/EP2016/063149
§ 371 (c)(1),
(2) Date: Dec. 14, 2017

(87) PCT Pub. No.: WO2017/008960
PCT Pub. Date: Jan. 19, 2017

(65) Prior Publication Data
US 2018/0353679 A1    Dec. 13, 2018

(30) Foreign Application Priority Data
Jul. 10, 2015 (EP) .................................... 15306140

(51) Int. Cl.
*A61M 5/168* (2006.01)
*A61M 5/145* (2006.01)

(52) U.S. Cl.
CPC ...... *A61M 5/16854* (2013.01); *A61M 5/1452* (2013.01); *A61M 5/16831* (2013.01);
(Continued)

(58) Field of Classification Search
CPC ............ A61M 5/16854; A61M 5/1452; A61M 5/16831; A61M 2205/332; A61M 2005/16863; A61M 2005/16868
See application file for complete search history.

(56) References Cited

U.S. PATENT DOCUMENTS 6,368,314 B1 * 4/2002 Kipfer ............... A61M 5/14546
222/309
2013/0237953 A1    9/2013 Kow et al.

FOREIGN PATENT DOCUMENTS

DE    198 40 992 A1    3/2000
JP    2012-034820 A    2/2012
(Continued)

OTHER PUBLICATIONS

International Search Report and Written Opinion, counterpart International Appl. No. PCT/EP2016/063149, dated Nov. 4, 2016 (12 pages).

*Primary Examiner* — Bradley J Osinski
(74) *Attorney, Agent, or Firm* — Cool Alex Ltd.

(57) ABSTRACT

The invention relates to a method for detecting an occlusion in an infusion line (200) during an infusion process comprising the steps of receiving a periodically measured value of a force (F) that is applied by a pumping device (1) to push a liquid through the infusion line (200) and that is indicative of the pressure (P) in the infusion line (200), and subtracting from the measured force value (F) a frictional force component ($F_0$), that is indicative of a true frictional force, for correcting the measured force value (F) by the true frictional force. The method is characterized in that the value of the frictional force component ($F_0$) is periodically updated throughout the infusion process by applying an equation that comprises a term that takes into account the measured force (F).

14 Claims, 4 Drawing Sheets

Figure 1:
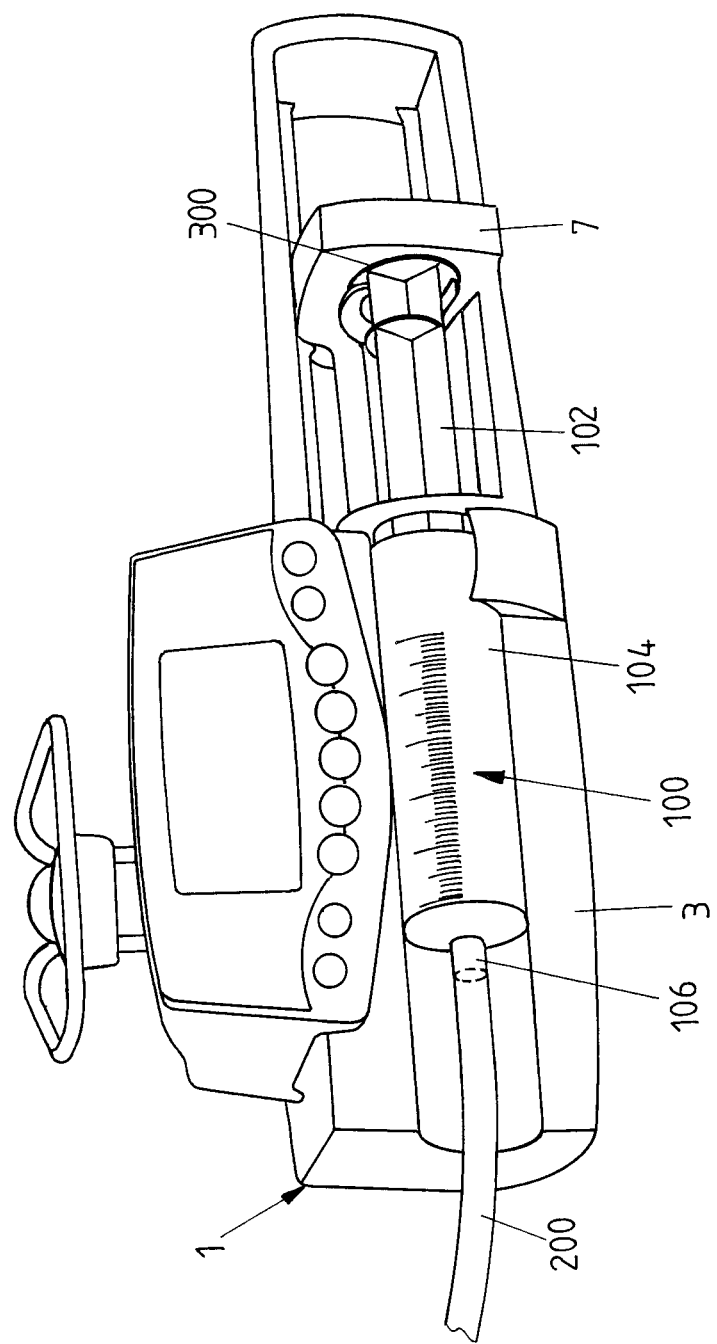

(52) U.S. Cl.
    CPC ............ *A61M 2005/16863* (2013.01); *A61M 2005/16868* (2013.01); *A61M 2205/332* (2013.01)

(56) References Cited

FOREIGN PATENT DOCUMENTS

| | | | |
|---|---|---|---|
| WO | WO2005/094919 A1 | 10/2005 |
| WO | WO2009/024562 A1 | 2/2009 |
| WO | WO2014/059006 A1 | 4/2014 |

\* cited by examiner

METHOD AND DEVICE FOR DETECTING AN OCCLUSION IN AN INFUSION LINE

The present application is a U.S. National Stage of PCT International Patent Application No. PCT/EP2016/063149, filed Jun. 9, 2016, which claims priority to EP Application No. 15306140, filed Jul. 10, 2015, both of which are hereby incorporated herein by reference The invention relates to a method for detecting an occlusion in an infusion line during an infusion process according to the preamble of claim 1.

Medication in a fluid state can be infused into a patient using an infusion line. The infusion line is connected to a fluid source such as a syringe that stores the medication. The medication can be pushed out of the syringe through the infusion line towards the patient using a syringe pump acting onto the syringe for continuously pushing a plunger into a cylindrical tube in order to deliver medication from the cylindrical tube of the syringe via the infusion line towards the patient.

During such an infusion process an occlusion may occur in the infusion line, which, in some cases, may cause severe injury to the patient. There hence is a need to reliably detect an occlusion occurring in an infusion line, in order to avoid injuries resulting from occluded infusion lines.

From the state of the art methods for detecting an occlusion in an infusion line during an infusion process are known that are based on the assumption that an occlusion causes a raise of the pressure in the infusion line. An increased pressure in turn causes the force to be applied to the syringe by a means of pumping device for pushing the medication through the infusion line towards the patient to increase. By monitoring the force applied to the syringe, hence, the actual pressure in the infusion line can be deduced. If the actual pressure exceeds a threshold value, an alarm signal indicative of an occlusion is triggered.

More sophisticated methods additionally take into account the frictional force of the syringe, such as the frictional force between the plunger and the cylindrical tube of the syringe, when the plunger is moving in the cylindrical tube. Indeed the total force required to push the liquid through an infusion line comprises a frictional force component, resulting from the friction occurring when the plunger is moved in the cylindrical tube, and a pressure component resulting from the pressure in the infusion line. In some methods known from the state of the art, the frictional force is assumed to be constant during the infusion process. For a given syringe type a constant value is then preset for the frictional force. For calculating the pressure inside the infusion line, hence, the force applied to the syringe is thus corrected for the frictional force using a constant value.

However, the frictional force is not necessarily constant for all syringes of a specific syringe type and/or throughout the entire infusion process, but can vary for example over the length of the cylindrical tube in which the plunger is longitudinally moved. For example, if the internal diameter of the cylindrical tube slightly decreases when moving the plunger in the cylindrical tube, the frictional force between the plunger and the inner wall of the cylindrical tube will increase and vice versa. In addition, the inner surface of the cylindrical tube may have varying characteristics over the length of the cylindrical tube. If the variation of the frictional force resulting therefrom is not taken into account and the true frictional force is higher than the preset (constant) value for the frictional force, the true pressure in the infusion line is smaller than the determined pressure. An overpressure may thus be detected which truly is not present, possibly leading to a false alarm signal. On the other hand, if the true frictional force is smaller than the preset (constant) value for the frictional force, the true pressure in the infusion line is higher than the determined pressure, in which case an overpressure resulting from an occlusion in the infusion line may not be detected.

The reliability of a method for detecting an occlusion that presumes that the frictional force component throughout the infusion process is constant is thus limited. However, a reliable method for detecting an occlusion may be of particular relevance, especially in neonate and pediatric care.

It is an object of the instant invention to provide a method for reliably detecting an occlusion in an infusion line during an infusion process.

This object is achieved by the method for detecting an occlusion in an infusion line during an infusion process comprising the features of claim 1.

Accordingly, a periodically measured value of a force that is applied by a pumping device to push a liquid through the infusion line and that is indicative of the pressure in the infusion line is received. The measured force is the total force that is applied, for example by a syringe pump, to push the liquid through the infusion line. This total force comprises one component resulting from the pressure in the infusion line and one component resulting from all non-pressure sources. The most relevant of these non-pressure sources is the friction that arises when pushing the liquid through the infusion line. In case of a syringe with a cylindrical tube and a plunger that is driven by a syringe pump, the non-pressure source is essentially the friction between the cylindrical tube and the plunger. This non-pressure source component shall be called frictional force component and is indicative of the true frictional force occurring when operating the pumping device, for example due to the frictional movement of the plunger within a cylindrical tube of the syringe.

The method according to the invention further provides to subtract from the measured force the frictional force component for correcting the measured force by the true frictional force. The measured force hence is corrected for the true frictional force by using a frictional force component that is periodically updated throughout the infusion process. One period for the periodical update herein may, in one embodiment, be defined as a position interval. This position interval is for example a finite, predefined length over which the plunger of the syringe, in which the liquid is stored, is moved by the pumping device or syringe pump, such that the periodical update occurs in a position dependent fashion.

For periodically updating the frictional force component the method applies an equation that comprises a term that takes into account the measured total force.

The method thus employs an estimated frictional force component which is periodically updated, allowing the method to determine the pressure in the infusion line more precisely. The updating may be used to distinguish variations of the total force essentially caused by a variation of the true frictional force variations of the total force caused by an occlusion in the infusion line. In this way, an overpressure resulting from an occlusion can be detected more reliably. Furthermore, in case of an occlusion the value of the pressure in the infusion line during the occlusion can be determined with a higher accuracy. The user can thus reliably deduce from the pressure in the occluded line the impact of the occlusion on the patient's physiological condition.

In one embodiment, for periodically updating the frictional force component the following equation is used: $F_0(n_i)=k_1F_0(n_{i-1})+k_2F(n_i)$, wherein $F_0(n_i)$ is the frictional force component ($F_0$) at a pumping position ($n_i$), $F_0(n_{i-1})$ is the frictional force component ($F_0$) at a precedent pumping position ($n_{i-1}$), $F(n_i)$ is the measured force (F) at the pumping position ($n_i$), and $k_1$ and $k_2$ are system dependent parameters with $k_1+k_2=1$.

The pumping position shall be a specific position of a pushing device that pushes the liquid through the infusion line. The equation may be applied every time said pushing device has reached a specific pumping position. The period between two subsequent updates of the frictional force component shall be $n_i-n_{i-1}$. For example, the period $n_i-n_{i-1}$ may be chosen to be smaller than 1 mm, for example 1/100 mm. That means every time the pushing device has moved by for example 1/100 mm, the equation $F_0(n_i)=k_1F_0(n_{i-1})+k_2F(n_i)$ is applied in order to update the value of the frictional force component.

The pushing device may be a plunger of a syringe or a pusher arm of a syringe pump.

For the equation $F_0(n_i)=k_1F_0(n_{i-1})+k_2F(n_i)$ weighing factors (or parameters) $k_1$ and $k_2$ can be chosen in dependence of the system the method is applied for. In particular, the parameters $k_1$ and $k_2$ may be dependent on the dimensions, such as length, diameter, volume, of a syringe in which the liquid to be pushed through the infusion line is stored. Essentially the parameters $k_1$ and $k_2$ may be chosen such that the value of the frictional force component evolves clearly differently for the case of an occlusion and for the case of a variation of the true frictional force only.

For example, the parameters $k_1$ and $k_2$ may be chosen such that in case of a variation of the measured force caused by a variation of the true frictional force, the frictional force component converges to the value of the measured force by applying the equation $F_0(n_i)=k_1F_0(n_{i-1})+k_2F(n_i)$. Alternatively, in case of a variation of the measured force caused by an occlusion in the infusion line, the frictional force component may not converge to the measured force by applying said equation.

Furthermore, the parameters $k_1$ and $k_2$ may be chosen such that, in case of a variation of the measured force caused by a variation of the true frictional force only, the difference between the measured force and the frictional force component does not exceed a predetermined threshold value. In case of a variation of the measured force caused by an occlusion in the infusion line, the difference between the measured force and the frictional force component may exceed said predetermined threshold value.

The difference between the measured force and the frictional force component is the measured force that has been corrected for the true frictional force. This difference can be used to calculate the pressure in the infusion line. Therefore, the parameters $k_1$ and $k_2$ may also be chosen such that in case only the frictional force varies (but not the pressure in the infusion line), the calculated pressure does not exceed a first predetermined pressure threshold value and that, in case of an occlusion in the infusion line, the calculated pressure exceeds the first predetermined pressure threshold value.

In one embodiment of the method the periodical determination of the frictional force component may be stopped and the frictional force component may be kept constant in case of an occlusion, i.e. if the calculated pressure exceeds the first predetermined pressure threshold value. This measure has the advantage that the value of the frictional force component stops increasing artificially by application of the equation $F_0(n_i)=k_1F_0(n_{i-1})+k_2F(n_i)$ when an occlusion has already been determined. In case of an occlusion the accuracy of the pressure determined in the infusion line may thus be increased.

The method may comprise further steps. For example, the method may include a step for calculating the pressure in the infusion line according to the equation $$P(n_i) = \frac{F(n_i) - F_0(n_i)}{S},$$

wherein $P(n_i)$ is the pressure at the pumping position $n_i$, $F(n_i)$ is the measured force F at the pumping position $n_i$, $F_0(n_i)$ is the frictional force component $F_0$ at the pumping position $n_i$, and S is a relevant surface of the pushing device that pushes the liquid through the infusion line.

If the method is used for a syringe with a plunger that is pushed by a syringe pump, the relevant surface S is thus the surface of the plunger that faces the liquid in the syringe and that transmits the force provided by (a motor of) the syringe pump to the liquid. In a first approach this relevant surface may be considered as constant throughout the entire infusion process.

As already described above, the method may provide a comparison of the calculated pressure with a predetermined pressure threshold value. In dependence of the outcome of the comparison, the periodical determination of the frictional force constant may be stopped, but also an alarm signal may be triggered. In particular, the method may provide a comparison of the calculated pressure with a first predetermined pressure threshold value and with a second predetermined pressure threshold value being larger than the first predetermined pressure threshold value. The first pressure threshold value may be chosen to lie between 10 and 30 mbar, preferably to be about 20 mbar. The second pressure threshold value typically lies between 60 and 1400 mbar, preferably between 66 and 1200 mbar. The periodical determination of the frictional force constant may be stopped, if the calculated pressure reaches (exceeds) the first predetermined pressure threshold value. The alarm signal may be triggered if the calculated pressure reaches (exceeds) the second pressure threshold value in order to indicate to a user that an occlusion has occurred. In case that the occlusion disappears before the calculated pressure exceeds the second pressure threshold value, the calculated pressure will drop and an alarm signal will not be triggered. The alarm signal may be an acoustic signal and/or a notification on a display.

In one embodiment, the method further comprises the step of periodically measuring with a force sensor the force that is applied by the pumping device to push the liquid through the infusion line and that is indicative of the pressure in the infusion line.

In another aspect, a device for detecting an occlusion in an infusion line during an infusion process comprises a processor that is configured to carry out the method according to the invention. The processor is adapted to receive a value of a force that is applied by a pumping device to push the liquid through the infusion line and that is indicative of the pressure in the infusion line. The detection device may be a separate element that may be connected to a pumping device, in particular to a syringe pump. In this case the processor of the detection device is connectable to the processor of the pumping device. The detection device may be located remotely from the pumping device, for example at a central location from where a plurality of pumping devices are surveyed and controlled.

The detection device may further comprise a force sensor adapted to periodically measure the force that is applied by the pumping device to push the liquid through the infusion line and that is indicative of the pressure in the infusion line. The force sensor may be adapted to communicate with the processor of the detection device. The force sensor is preferably arranged at the pumping device. For example, the force sensor may be arranged at the pumping device at that point at which the pumping device transmits the force for pushing the liquid through the infusion line to a syringe.

In one embodiment, a signaling device for emitting an alarm signal is provided that is connected to the processor of the detection device. The signaling device may be located remotely from the processor (and the force sensor), for example at a central location from where a plurality of detection devices and/or pumping devices are surveyed.

In yet another aspect, said device may be part of a syringe pump.

Figure 2:
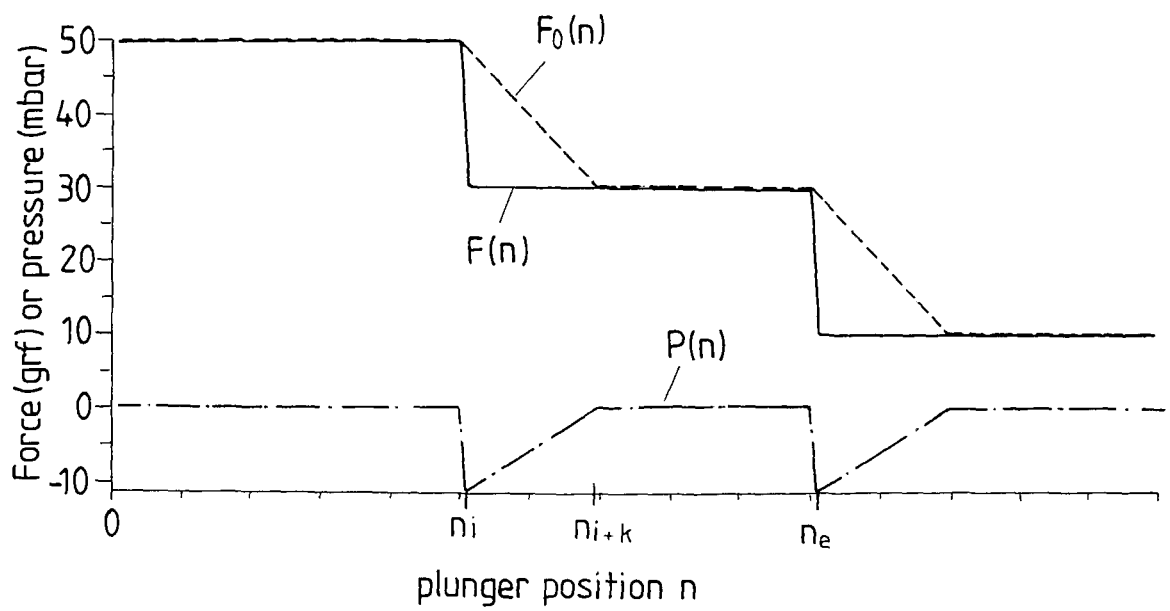
Figure 3:
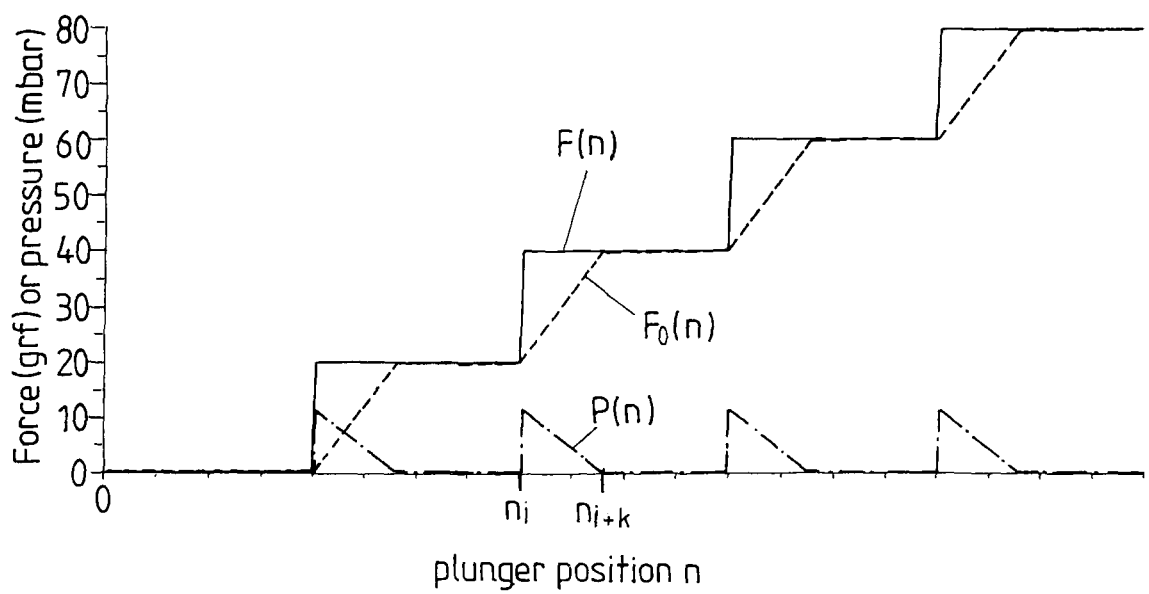
Figure 4:
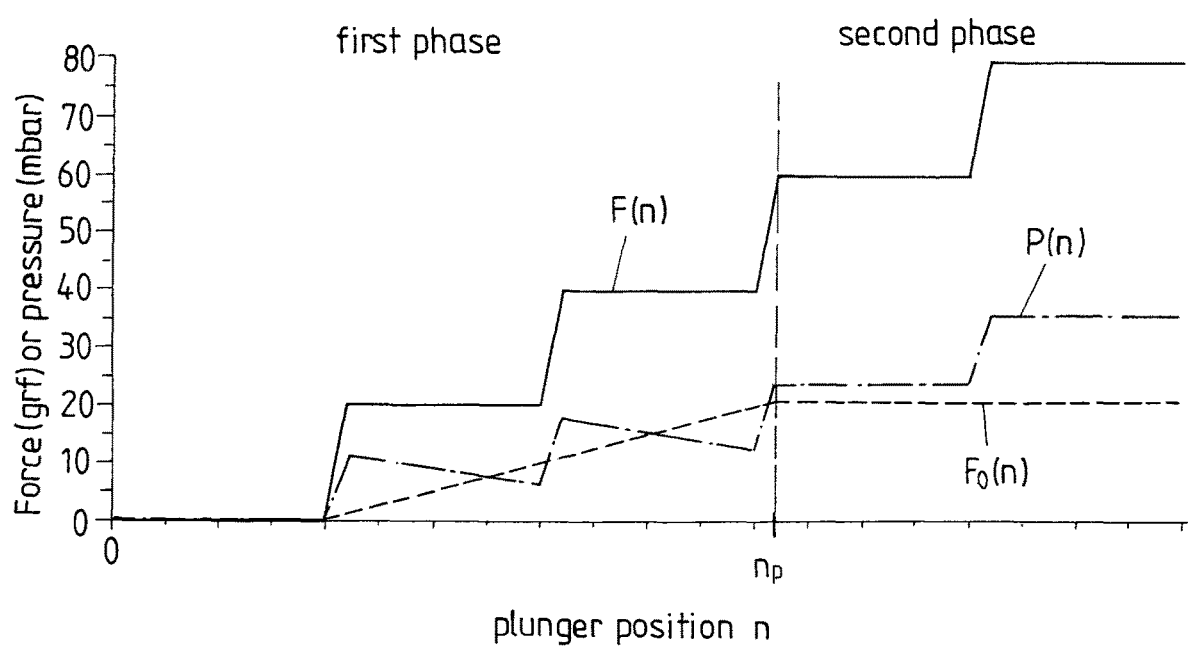
Figure 5:
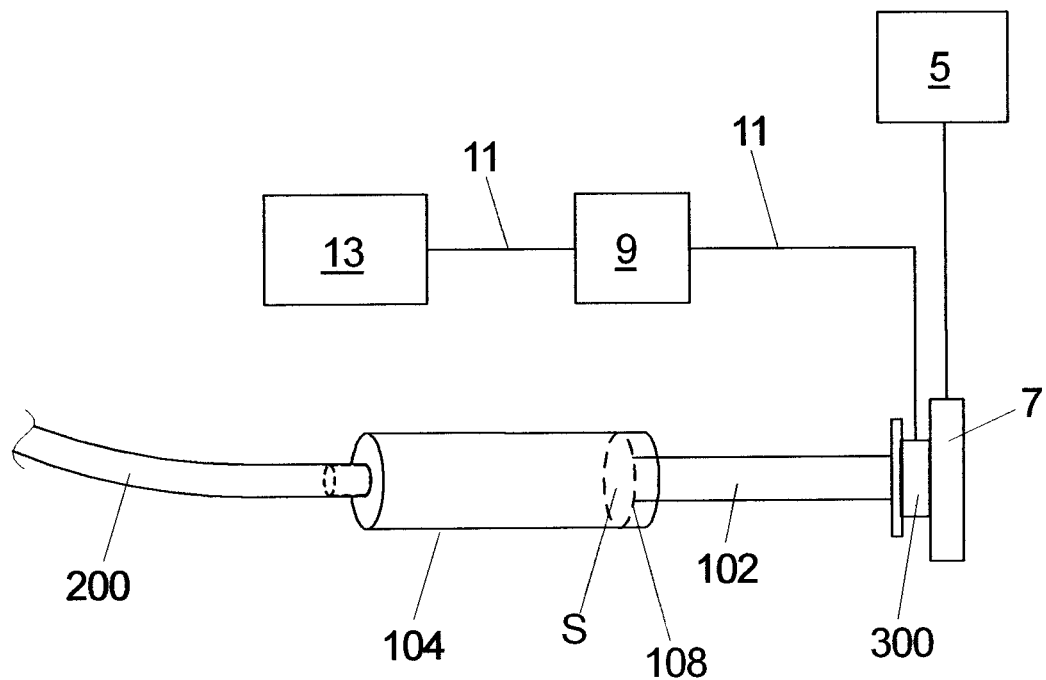

The idea underlying the invention shall subsequently be described in more detail with reference to the figures. Herein:

FIG. 1 exemplarily shows a syringe pump with a syringe and an infusion line connected to the syringe;

FIG. 2 schematically shows one example of a variation of a total force value (continuous line) resulting from a variation of the frictional force, as well as the evolution of the corresponding estimated frictional force value (dashed line) and of the estimated pressure (dash-dot line);

FIG. 3 schematically shows another example of a variation of the total force value (continuous line) resulting from a variation of the frictional force, as well as the evolution of the corresponding estimated frictional force value (dashed line) and of the estimated pressure (dash-dot line);

FIG. 4 schematically shows one example of a variation of the total force value (continuous line) resulting from an occlusion in the infusion line, as well as the evolution of the corresponding estimated frictional force value (dashed line) and of the estimated pressure (dash-dot line); and FIG. 5 schematically shows components of a syringe pump with a syringe connected to an infusion line.

FIG. 1 shows a syringe pump designated with the reference numeral 1 and holding a syringe 100.

The syringe 100 forms a reservoir for a medication and comprises a plunger 102 that is slidably arranged in a cylindrical tube 104 of the syringe 100. At a first axial end the cylindrical tube 104 is connected via a connector 106 to an infusion line 200. At a second axial end, opposite of the first axial end, the cylindrical tube 104 receives the plunger 102. The plunger 102 comprises a pushing surface 108 (FIG. 5) which is able to push the medication stored in the cylindrical tube 104 when the plunger 102 slides inside the cylindrical tube 104 in a direction from the second axial end towards the first axial end of the cylindrical tube 104.

The syringe pump 1 comprises a holding device 3 for properly arranging and holding the syringe 100 in an intended position, as shown in FIG. 1. The syringe pump 1 further comprises a motor 5 (FIG. 5) for driving a pusher arm 7 of the syringe pump 1. The pusher arm 7 is able to transmit a force F to the plunger 102 of the syringe 100 to push the medication from the syringe 100 through the infusion line 200 towards a patient.

On a face of the pusher arm 7, which is oriented towards the plunger 102 of the syringe 100, a force sensor 300 is arranged (FIG. 5). If the syringe 100 is arranged in its intended position, the force sensor 300 is located between the plunger 102 and the pusher arm 7 and is adapted to measure the force F that the pusher arm 7 transmits to the plunger 102. The force sensor 300 may be integral with the pusher arm 7 or may be constituted as a separate element.

Furthermore, a processor 9 (FIG. 5) is provided that may be arranged in the housing of the syringe pump 1 or may be part of a separate device. The processor 9 is connected to the force sensor 300 via a communication line 11 and is configured to carry out a method for detecting an occlusion in the infusion line 200 connected to the syringe 100. Once an occlusion is detected, the processor 9 triggers an alarm signal that is emitted by a signaling device 13. The signaling device 13 is connected to the processor 9 via another communication line 11. Again, the signaling device 13 may be arranged in the housing of the syringe pump 1 or may be an external device.

In the following, an embodiment of a method for detecting an occlusion in an infusion line will be described.

An occlusion in the infusion line 200 causes a pressure P in the infusion line 200 to increase if the pusher arm 7 keeps pushing the plunger 102 into the cylindrical tube 104. Accordingly, if the pressure P is increased, the force F applied by the motor 5 (or by the pusher arm 7) to the plunger 102 of the syringe 100 is also increased. This (total) force F, which can be measured by the force sensor 300, comprises a frictional force component $F_0$ due primarily to friction of the plunger 102 in the cylindrical tube 104 and a pressure component due to the pressure within the infusion line 200. In order to precisely determine the pressure, hence, not the total force F, but only the pressure component $F_0$ of the total force F has to be considered. Therefore, the total force F measured by the force sensor 300 needs to be corrected for the frictional force component $F_0$, so that the pressure P in the infusion line 200 can be determined according to the equation:

$$P = \frac{F - F_0}{S}.$$

In this equation S represents the effective surface area of the element that transmits the force F applied by the pusher arm 7 of the syringe pump 1 to the medication in the syringe 100. In the example shown in FIGS. 1 and 5, the surface S corresponds to the area of the pushing surface 108 of the plunger 102 within the cylindrical tube 104, the surface S being oriented substantially orthogonal with respect to the plunger's longitudinal axis.

The method requires that the total force F is periodically measured by the force sensor 300 and that the values of the total force F are transmitted to the processor 9. The force measurement is generally carried out over time at preset time intervals.

In the present method, the value of the frictional force component $F_0$ is not measured, but estimated (calculated). In particular, the value of the frictional force component $F_0$ is periodically updated. The update of the frictional force component $F_0$ herein is carried out periodically dependent on the plunger's 102 position, at steps (intervals) of for example 1/100 mm.

In a so-called steady state, the plunger 102 moves with a constant speed inside the cylindrical tube 104, the speed determining the flow rate achieved with the syringe pump during operation. The time scale for the total force measurement and the plunger position scale for the update of the frictional force component $F_0$ are thus linearly correlated. It shall be assumed that the plunger 102 is in a specific plunger position $n_i$ at a specific point of time $t_i$. Thus, the force $F(t_i)$ measured at (or immediately prior) to the specific point of time $t_i$ is the force valid at the position $n_i$ and can be denoted as the force $F(n_i)$ at the specific plunger position $n_i$.

In the following, the plunger position will be denoted as "n" when the plunger position in general is concerned. However, if reference is made to a specific plunger position additionally an index will be used, for example $n_i$.

The periodical update of the frictional force component $F_0$ provides at every interval (every $\frac{1}{100}$ mm) a corresponding estimated value of the frictional force component $F_0(n_i)$.

For updating the frictional force component $F_0$ in order to obtain the specific frictional force component $F_0(n_i)$ at the plunger position $n_i$ an equation is applied that comprises a term that takes into account the total force F at the plunger position $n_i$.

The equation takes furthermore into account the value of the preceding frictional force component $F_0(n_{i-1})$ at the plunger position $n_{i-1}$ (the plunger position $n_i$ shall be the plunger position that directly follows the plunger position $n_{i-1}$ and that is separated from the plunger position $n_{i-1}$ by the update interval of for example $\frac{1}{100}$ mm).

In particular, the equation for determining the value of the frictional force component $F_0(n_i)$ reads:

$$F_0(n_i) = k_1 F_0(n_{i-1}) + k_2 F(n_i),$$

wherein $F_0(n_i)$ is the frictional force component $F_0$ at the plunger position $n_i$, $F_0(n_{i-1})$ is the frictional force component $F_0$ at the precedent plunger position $n_{i-1}$, $F(n_i)$ is the total measured force F valid at the plunger position $n_i$ (or measured at the point of time $t_i$), and $k_1$ and $k_2$ are system dependent parameters with $k_1 + k_2 = 1$.

This equation corresponds to the mathematical representation of a first order Infinite Impulse Response (IIR) filter. At the beginning, the very first value of the frictional force component $F_0(n_0)$ is initialized by setting it to be equal to the total measured force $F(n_0)$ at the very first plunger position $n_0$.

The parameters $k_1$ and $k_2$ are carefully chosen in dependence of the syringe 100 that is actually used for delivering medication to a patient. For example, for a syringe 100 with a volume of 50 cm³ $k_1$ may be set for example to a value between 0.90 and 0.99, in particular 0.97 or 0.98 (wherein $k_2$ is equal to $1-k_1$). The values of $k_1$ and $k_2$ may for example be determined in an initial calibration sequence prior to the actual operation of the syringe pump 1 by evaluating the convergence behaviour of the above noted update equation.

After the frictional force component $F_0(n_i)$ has been determined for the plunger position $n_i$ by using the equation $F_0(n_i) = k_1 F_0(n_{i-1}) + k_2 F(n_i)$, the pressure P is determined for the plunger position $n_i$ using the equation:

$$P(n_i) = \frac{F(n_i) - F_0(n_i)}{S}.$$

Herein, S is again the effective surface area of the pushing surface 108 of the plunger 102.

Once the pressure $P(n_i)$ has been determined, the pressure $P(n_i)$ is compared with a first predetermined pressure threshold value $P_{occ}$. If the estimated pressure $P(n_i)$ is below the first predetermined pressure threshold value $P_{occ}$, it is considered that a variation of the true frictional force component is the origin of the variation of the total force F. It is therefore considered appropriate to continue to periodically update the estimated frictional force component $F_0$. The above steps are thus repeated: the next frictional force component $F_0(n_{i+1})$ is determined, and again the estimated pressure $P(n_{i+1})$ is compared with the first predetermined pressure threshold value $P_{occ}$, and so on.

If indeed no occlusion is present and if the update equation is correctly calibrated by choosing the $k_1$ and $k_2$ values, the estimated pressure P will remain below the first predetermined pressure threshold value $P_{occ}$, and upon a variation of the measured force F the frictional force component $F_0$ will eventually converge to the measured total force F.

If on the other hand at some plunger position $n_{i+x}$ the estimated pressure $P(n_{i+x})$ exceeds the first predetermined pressure threshold value $P_{occ}$, the value of the frictional force component $F_0$ is no longer updated. In this case it is considered that the variation of the frictional force component is not the origin of the variation of the total force $F(n)$ and that it is therefore improper to further update the value of the estimated frictional force component $F_0(n)$. The estimated frictional force component $F_0(n)$ is then kept constant and is fixed to the last updated value of $F_0(n_{i+x})$ while the total force F is further monitored. Also, the estimated pressure P is further updated using the measured total force F and the constant frictional force component $F_0(n_{i+x})$. An alarm signal is triggered if the estimated pressure P exceeds a second predetermined pressure threshold value $P_{occ}$ set by the user. The first predetermined pressure threshold value $P_{occ}$ is typically between 10 and 30 mbar, preferably about 20 mbar. The second predetermined pressure threshold value $P_{occ}$ is typically between 60 and 1400 mbar, preferably between 66 and 1200 mbar. In any case the first predetermined pressure threshold value $P_{occ}$ is lower than the second predetermined pressure threshold value $P_{occ}$.

As subsequently shall be illustrated with reference to FIGS. 2 to 4, by properly choosing the values of the parameters $k_1$ and $k_2$, the method is able to distinguish between two events, each of which leads to a variation of the total force F measured by the force sensor 300:

a) The true frictional force component changes and causes a variation of the total force F (FIGS. 2 and 3).

b) An occlusion occurs in the infusion line 200 and causes a variation of the total force F (FIG. 4).

In case a) the variation of the total force $F(n)$ may exhibit a decrease of the measured force $F(n)$ (FIG. 2) or an increase of the measured force $F(n)$. While in case a) the variation of the measured force $F(n)$ is typically relatively small and occurs on a long time scale, in case b) a significant increase of the measured force $F(n)$ can be observed. As typical for an occlusion, the increase of the measured force $F(n)$ is observed on a short time scale.

In FIG. 2 the continuous line indicates by way of example the evolution of the value of the measured total force $F(n)$ as a function of the plunger position n in case a), i.e., without an occlusion being present. In the example shown in FIG. 2, the measured total force $F(n)$ shows two steps at the plunger positions $n_i$ and $n_j$, each step indicating a decrease of the force $F(n)$. Such a situation may be observed for example when the inner diameter of the cylindrical tube 104 of the syringe 100 slightly increases and the friction between the inner surface of the cylindrical tube 104 and the plunger 102 of the syringe 100 is reduced. By applying the equation $$F_0(n_i) = k_1 F_0(n_{i-1}) + k_2 F(n_i),$$

at every position interval (of for example ¹/₁₀₀ mm) the frictional force component $F_0(n)$ is newly determined, shown in FIG. 2 as a dashed line.

Initially, the frictional force component $F_0(n)$ is equal to the measured force $F(n)$. Upon a variation in the measure force, for example the step at plunger position $n_i$, the frictional force component $F_0(n)$ decreases after the step in the measured force $F(n)$ has occurred and converges towards the measured force $F(n)$ at a convergence rate determined by the parameters $k_1$ and $k_2$. At some plunger position $n_{i+k}$ the value of the frictional force component $F_0$ has converged to the measured force $F(n_{i+k})$.

Additionally, the evolution of the pressure P, which is determined by using the equation $$P(n_i) = \frac{F(n_i) - F_0(n_i)}{S},$$

as a function of the plunger position n is shown in FIG. 2 as a dash-dot line. Initially the pressure is zero, due to $F(n)$ and $F_0(n)$ being equal. For example at the plunger position $n_i$ (at which a step occurs in the measured force signal $F(n)$) the value of the pressure $P(n)$ falls to a minimum and then increases as the value of the frictional force component $F_0(n)$ converges to the measured force $F(n_{i+k})$. The step in the measured force signal $F(n)$ hence causes a negative pressure estimate. However, when the value of the frictional force component $F_0(n)$ has converged at $n_{i+k}$ to the measured force $F(n_{i+k})$, the estimated pressure P again becomes zero.

FIG. 3 shows another example for case a). In FIG. 3, the measured total force $F(n)$ shows four steps, each step indicating an increase of the force $F(n)$. Such a situation may be observed for example when the inner diameter of the cylindrical tube 104 of the syringe 100 slightly decreases and the friction of the plunger 102 within the cylindrical tube 104 of the syringe 100 thus increases. The evolution of the frictional force component $F_0(n)$ (determined by applying the equation $F_0(n_i)=k_1 F_0(n_{i-1})+k_2 F(n_i)$) as a function of the plunger position n is shown in FIG. 3 again as a dashed line. It can be seen that the value of the frictional force component $F_0(n)$ rises after the step has occurred in the measured force signal $F(n)$ at $n_i$ and, as already seen in FIG. 2, converges towards the measured force $F(n)$. Also the evolution of the pressure, shown in FIG. 3 as a dash-dot line, is qualitatively comparable (but opposite) to the pressure evolution in FIG. 2. At the plunger position $n_i$ at which the step occurs in the measured force signal $F(n)$, the value of the pressure $P(n)$ first rises to a maximum and then decreases as the value of the frictional force component $F_0(n)$ converges to the measured force $F(n)$. The step in the measured force signal $F(n)$ hence is first seen as a positive pressure estimate. However, when the value of the frictional force component $F_0(n)$ has converged to the measured force $F(n)$, the pressure estimate P becomes zero.

In the examples shown in FIGS. 2 and 3 the absolute value of the determined pressure $P(n)$ is always below the first predetermined pressure threshold value $P_{occ}$, set to for example 20 mbar. As the absolute value of the determined pressure $P(n)$ is also always below the second predetermined pressure threshold value $P_{occ}$, no alarm signal is triggered.

In FIG. 4 an occlusion case (case b)) is shown. The continuous line indicates exemplarily the evolution of the value of the measured total force $F(n)$ as a function of the plunger position n. In the example shown in FIG. 4, the measured total force $F(n)$ shows four steps in comparatively rapid succession, each step indicating an increase of the total force $F(n)$. The evolution of the frictional force component $F_0(n)$ as a function of the plunger position n is shown in FIG. 4 as a dashed line. The evolution of the pressure $P(n)$ as a function of the plunger position n is shown as a dash-dot line. The first pressure threshold value $P_{occ}$ is set to 20 mbar in this example.

In FIG. 4 the frictional force component $F_0(n)$ and the pressure $P(n)$ each pass through two phases, the transition from the one phase into the other indicated in FIG. 4 by a vertical dashed line being determined by the first pressure threshold value $P_{occ}$.

In the first phase the value of the frictional force component $F_0(n)$ is periodically updated as the value of the corresponding pressure $P(n)$ is below the first pressure threshold value $P_{occ}$. It can be seen that the value of the frictional force component $F_0(n)$ increases linearly in the first phase. However, the measured total force $F(n)$ increases more rapidly than the (continuously updated) frictional force component $F_0(n)$, such that the frictional force component $F_0(n)$ cannot converge to the measured total force $F(n)$.

This causes also the pressure estimate P to keep rising. Generally, when a step occurs in the measured total force $F(n)$, the pressure $P(n)$ first increases and then slightly decreases, but as the frictional force component $F_0(n)$ does not converge to the measured total force $F(n)$ the pressure $P(n)$ does not converge to zero. At the plunger position $n_p$, instead, the pressure $P(n_p)$ reaches the first pressure threshold value $P_{occ}$.

At this point the second phase is entered. At this point it is considered that the variation of the measured total force $F(n)$ does not arise from a variation of the frictional force component and that it is improper to further update the value of the (estimated) frictional force component $F_0(n)$. The value of the frictional force component $F_0(n)$ hence is no longer updated, but it is kept constant at the level of the last value $F_0(n_p)$ at the end of the first phase.

Meanwhile, the total force $F(n)$ is further measured and also the pressure $P(n)$ is further calculated. As the value of the frictional force component $F_0(n)$ is kept constant in the second phase and as the measured force signal $F(n)$ continues to rise, the pressure $P(n)$ rises as well and follows the evolution of the measured force signal $F(n)$.

After a further pressure increase in the second phase and when the pressure $P(n)$ has reached the second pressure threshold value $P_{occ}$ (a pressure value typically between 66 and 1200 mbar, depending on the user's settings) an alarm signal is triggered. Between triggering the alarm signal and stopping the syringe pump 1 a certain amount of time may pass. As the pressure $P(n)$ is further calculated during the second phase, the user can be informed about the pressure in the infusion line 200 at the moment of stopping the syringe pump 1.

In general, the value of the frictional force component $F_0(n_p)$ at the plunger position $n_p$ at which the alarm is triggered will not correspond to the value of the frictional force component $F_0(n)$ at the beginning of the occlusion. Indeed the value of the frictional force component $F_0(n_p)$ at the moment at which the alarm is triggered is larger than the value of the frictional force component $F_0(n)$ at the beginning of the occlusion, because it has been updated over a multiplicity of intervals until the first threshold $P_{occ}$ was reached. Therefore, the estimated pressure will be smaller than the true pressure in the infusion line 200 when the alarm is triggered. This offset may be compensated for by lowering the second predetermined pressure threshold value $P_{occ}$ relevant for triggering the alarm signal so that an alarm is reliably triggered when the true pressure in the infusion line has reached a physiologically relevant pressure threshold.

The method can take further into account a particular situation during the infusion process. At the very beginning of an infusion process while starting to move the plunger 102, during a transient state the frictional force may increase strongly as the plunger 102 is accelerated, until a steady state is reached in which the plunger 102 is moved with a constant speed. In the transient state an increase of the total force F(n) is usually observed that may be comparable in intensity to an occlusion case. A strong increase of the total force F(n) at the very beginning of the infusion during the transient state may thus be misleadingly interpreted as an occlusion.

Hence, during the transient state the value of the frictional force component $F_0(n)$ can be updated such that it is close or equal to the measured force signal F(n). The corresponding estimated pressure P(n) is thus low or zero. In any case, the pressure P(n) is below the second predetermined pressure threshold value $P_{occ}$, so that no alarm signal is triggered during the transient state.

The transient state may last for example for approximately 1 mm at the beginning of the movement of the plunger 102.

In the example given, the plunger speed is constant during the steady state. In case the plunger speed needs to be changed during the infusion process, for example in case the infusion rate needs to be adjusted, a new transient state can be started every time the plunger speed is changed. Once steady state is again reached, the noted update equation $F_0(n_i)=k_1 F_0(n_{i-1})+k_2 F(n_i)$ is used for periodically updating the frictional force component $F_0(n)$, the equation being the same for different plunger speeds, in particular using the same parameters $k_1$ and $k_2$.

The invention claimed is:

1. A method for detecting an occlusion in an infusion line during an infusion process, the method comprising:
   receiving a periodically measured value of a force that is applied by a pumping device to push a liquid through the infusion line and that is indicative of the pressure in the infusion line, and
   subtracting from the measured force value a frictional force component, that is indicative of a true frictional force, for correcting the measured force value by the true frictional force,
   wherein the value of the frictional force component is periodically updated throughout the infusion process by applying an equation that comprises a term that takes into account the measured force value,
   wherein the equation for determining the frictional force component at a specific pumping position of the pumping device is:

$F_0(n_i)=k_1 F_0(n_{i-1})+k_2 F(n_i)$, wherein
   $F_0(n_i)$ is the frictional force component at the pumping position,
   $F_0(n_{i-1})$ is the frictional force component at a preceding pumping position,
   $F(n_i)$ is the measured force value at the pumping position, and
   $k_1$ and $k_2$ are system dependent parameters with $k_1+k_2=1$.

2. The method according to claim 1, wherein the parameters $k_1$ and $k_2$ are chosen such that in case of a variation of the measured force value resulting from a variation of the true frictional force, the frictional force component converges to the measured force value when applying the equation $F_0(n_i)=k_1 F_0(n_{i-1})+k_2 F(n_i)$ and that, in case of a variation of the measured force value resulting from an occlusion in the infusion line, the frictional force component does not converge to the measured force value when applying the equation $F_0(n_i)=k_1 F_0(n_{i-1})+k_2 F(n_i)$.

3. The method according to claim 1, wherein the parameters $k_1$ and $k_2$ are chosen such that, in case of a variation of the measured force value resulting from a variation of the true frictional force, a difference between the measured force value and the frictional force component does not exceed a predetermined threshold value and that, in case of a variation of the measured force value resulting from an occlusion in the infusion line, the difference between the measured force value and the frictional force component does exceed the predetermined threshold value.

4. The method according to claim 3, wherein, in case that the difference between the measured force value and the frictional force component does exceed the predetermined threshold value, the periodical updating of the frictional force component is stopped and the frictional force component is kept constant.

5. The method according to claim 1, further comprising:
   calculating the pressure at the pumping position in the infusion line according to $$P(n_i) = \frac{F(n_i) - F_0(n_i)}{S}$$

wherein $P(n_i)$ is the pressure at the pumping position,
   $F(n_i)$ is the measured force value at the pumping position,
   $F_0(n_i)$ is the frictional force component at the pumping position, and
   S is a relevant surface of a pushing device that pushes the liquid through the infusion line, and
   comparing the calculated pressure with a predetermined pressure threshold value.

6. The method according to claim 5, further comprising triggering an alarm signal if the calculated pressure exceeds the pressure threshold value.

7. The method according to claim 5, wherein the relevant surface is considered as being constant throughout the infusion process.

8. The method according to claim 1, further comprising periodically measuring with a force sensor the force that is applied by the pumping device to push the liquid through the infusion line and that is indicative of the pressure in the infusion line.

9. A device for detecting an occlusion in an infusion line during an infusion process, comprising a processor configured to receive a value of a force that is applied by a pumping device to push a liquid through the infusion line and that is indicative of the pressure in the infusion line, wherein the processor is configured to carry out the method according to claim 1.

10. The device according to claim 9, further comprising a force sensor configured to periodically measure the force that is applied by the pumping device to push the liquid through the infusion line and that is indicative of the pressure in the infusion line, wherein the force sensor is configured to communicate with the processor.

11. The device according to claim 9, further comprising a signaling device connected to the processor and configured to emit an alarm signal.

12. A syringe pump comprising:
   a holding device for holding a syringe that can be coupled to an infusion line, a motor for acting on a plunger of the syringe for pushing a liquid stored in the syringe through the infusion line, and a processor configured to receive a value of a measured force that is applied by the motor to push the liquid through the infusion line and that is indicative of a pressure in the infusion line, wherein the processor is configured to carry out the method according to claim 1.

13. The syringe pump according to claim 12, further comprising a force sensor configured to periodically measure the force that is applied by the motor to the plunger to push the liquid through the infusion line and that is indicative of the pressure in the infusion line, wherein the force sensor is configured to communicate with the processor, and wherein the force sensor is arranged such that it is configured to measure the force at an end of the plunger at which the motor acts onto the plunger.

14. A non-transitory carrier medium carrying computer executable code that, when executed on a processor, causes said processor to perform the method according to claim 1.

* * * * *